US00PP08042P

United States Patent [19]

van der Knaap

[11] Patent Number: Plant 8,042

[45] Date of Patent: Nov. 24, 1992

[54] CHRYSANTHEMUM PLANT—ROYAL MUNDIAL CULTIVAR

[75] Inventor: Jacques C. M. van der Knaap, DeLier, Netherlands

[73] Assignee: Fides Beheer B.V., DeLier, Netherlands

[21] Appl. No.: 679,514

[22] Filed: Apr. 2, 1991

[51] Int. Cl.[5] ..... A01H 5/00

[52] U.S. Cl. ..... Plt./74.1

[58] Field of Search ..... Plt./74, 74.1, 82.4, Plt./76, 80, 81

*Primary Examiner*—Howard J. Locker

*Attorney, Agent, or Firm*—Burns, Doane, Swecker & Mathis

[57] ABSTRACT

A new and distinct cultivar of Chrysanthemum plant names Royal Mundial is provided. The new cultivar is a spontaneous mutation of the Mundial cultivar (U.S. plant patent application Ser. No. 679,528, filed concurrently herewith). More specifically, the new cultivar forms attractive relatively large purple anemone-centered flowers having a green center when immature. The inflorescence tends to be pyramidal in configuration. The response period of the flowers is approximately eight weeks. The new cultivar is particularly suited for use in the production of a cut anemone spray under greenhous conditions.

1 Drawing Sheet

SUMMARY OF THE INVENTION

The present invention comprises a new and distinct cultivar of Chrysanthemum, botanically known as *Dendranthema morifolium* Ramat., previously, *Chrysanthemum morifolium,* Ramat., and hereinafter is referred to by the cultivar name Royal Mundial.

The new cultivar is a spontaneous mutation of unknown causation which was discovered during December, 1987 during the course of plant selection work which was conducted by me. The new cultivar was discovered among plants of the Mundial cultivar (U.S. plant patent application Ser. No. 679,528, filed concurrently herewith) being grown under my direct supervision at De Lier, The Netherlands, which formed blossoms having ray florets possessing the characteristic light red-purple coloration.

It was observed that a single plant consistently formed flowers having ray florets of a distinctive purple coloration. All of the other characteristics of this plant were found to be substantially identical to those of the Mundial cultivar. Had I not discovered, carefully studied, and preserved this new cultivar it would have been lost to mankind. This new cultivar is particularly well suited for growing in the production of a cut anemone spray.

It was found that the new cultivar of the present invention:

(a) exhibits attractive relatively large anemone-centered flowers having an overall diameter of approximately 75 to 80 mm. wherein the ray florets are purple and the disc florets are green in coloration when immature,
(b) bears flowers in a somewhat pyramidal configuration,
(c) exhibits a flower response period of approximately eight weeks, and
(d) has the ability to produce flowers of commercially acceptable quality throughout the year in a cut mum production program.

Asexual reproduction of the new cultivar by cuttings as performed at De Lier, The Netherlands, in a controlled environment has demonstrated that the characteristics of the new cultivar as herein disclosed are firmly fixed and are retained through successive generations of asexual propagation.

Royal Mundial has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the parent Mundial cultivar (U.S. plant patent application Ser. No. 679,528, filed concurrently herewith), it is found to exhibit a distinctive purple floret coloration unlike the light red-purple floret coloration of its parent. Also, such floret coloration can be readily distinguished from the additional mutation of the Mundial cultivar named Bronze Mundial (U.S. plant patent application Ser. No. 679,513, filed concurrently herewith) which exhibits yellow-orange florets.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is the R.H.S. Colour Chart of The Royal Horticulatural Society, London, England. The color values were determined at 11:00 a.m. to 12:00 noon under natural daylight conditions at De Lier, The Netherlands, during November, 1989. The plants described were grown under standard greenhouse conditions which approximate those commonly utilized for the production of cut mums.

Classification:

*Botanical.—Dendranthema morifolium* Ramat., cv. Royal Mundial.

*Commercial.*—Cut anemone spray.

Inflorescence

A. Capitulum:
*Form.*—Pyramidal.
*Type.*—Anemone.
*Diameter across face.*—Approximately 75 to 80 mm. on average.
*Diameter of disc.*—Approximately 22 to 30 mm. on average.

B. Corolla of ray and disc florets:
*Color (General tonality from a distance of three meter).*—Purple.
*Color ray florets.*—(Top surface). — Red-Purple Group 68B. (Under surface). — Red-Purple Group 68C.
*Color disc florets.*—Green Group 142A when immature.

C. Reproductive organs:
*Androecium.*—Not present.
*Gynoecium.*—Present in disc florets.

Plant

A. General appearance:

*Height.*—Approximately 100 cm. on average.

B. Foliage:
*Color (upper surface).*—Yellow-Green Group 147A.
*Color (under surface).*—Yellow-Green Group 147B.

I claim:

1. A new and distinct cultivar of Chrysanthemum plant named Royal Mundial, substantially as herein shown and described, which:

(a) exhibits attractive relatively large anemone-centered flowers having an overall diameter of approximately 75 to 80 mm. wherein the ray florets are purple and the disc florets are green in coloration when immature,
(b) bears flowers in a somewhat pyramidal configuration,
(c) exhibits a flower response period of approximately eight weeks, and
(d) has the ability to produce flowers of commercially acceptable quality throughout the year in a cut mum production program.

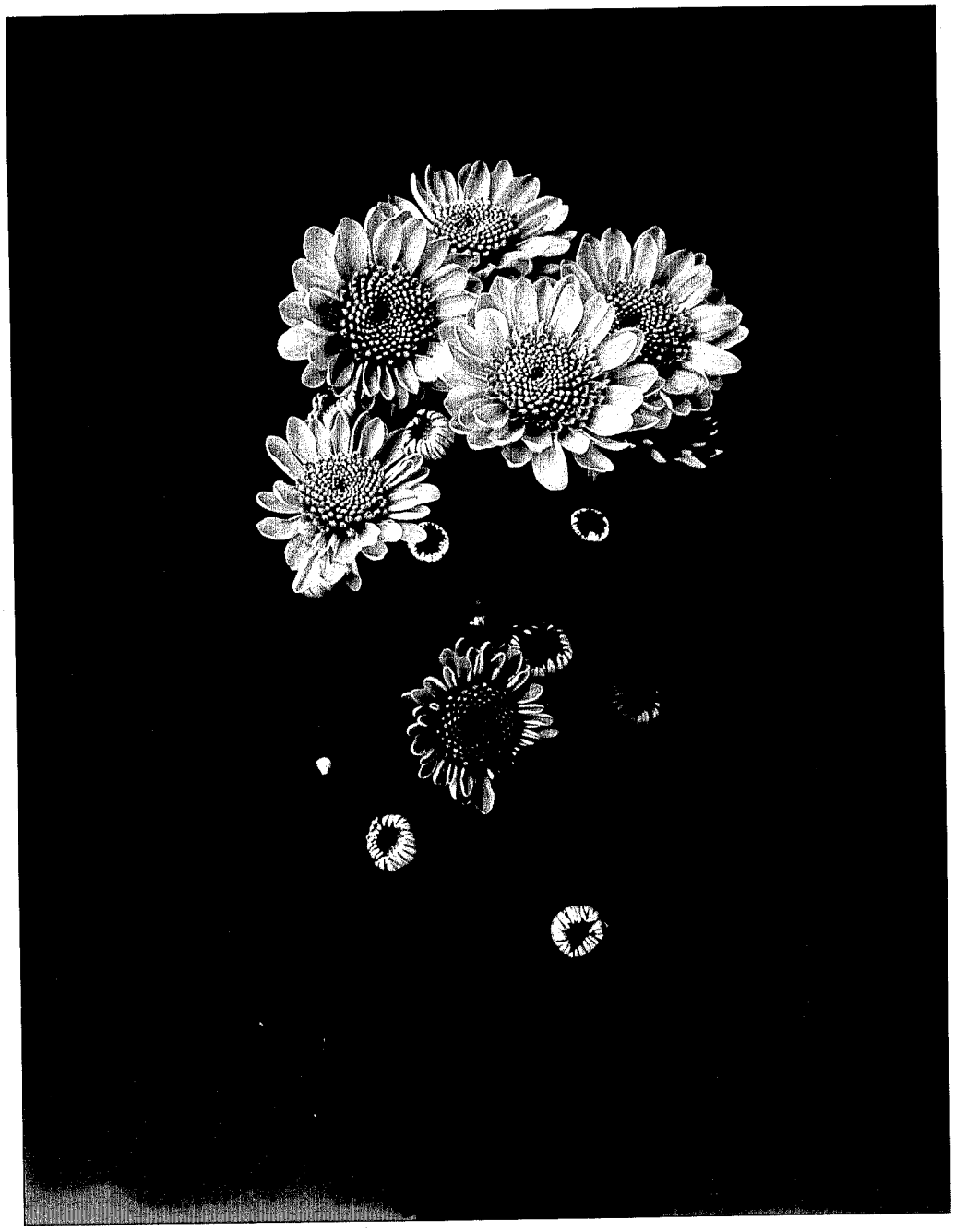

* * * * *